(12) United States Patent
Ellis

(10) Patent No.: US 9,078,670 B2
(45) Date of Patent: *Jul. 14, 2015

(54) DRILL BIT

(75) Inventor: Liam Patrick Ellis, Blackalls Park (AU)

(73) Assignee: CPL HOLDINGS PTY. LTD., Blackalls Park (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/989,357

(22) PCT Filed: Nov. 25, 2011

(86) PCT No.: PCT/AU2011/001539
§ 371 (c)(1),
(2), (4) Date: May 23, 2013

(87) PCT Pub. No.: WO2012/068641
PCT Pub. Date: May 31, 2012

(65) Prior Publication Data
US 2013/0253521 A1    Sep. 26, 2013

(30) Foreign Application Priority Data

Nov. 26, 2010 (AU) .................. 2010905238
Feb. 11, 2011 (AU) .................. 2011900459
Jun. 23, 2011 (AU) .................. 2011902465

(51) Int. Cl.
*A61B 17/00* (2006.01)
*A61B 17/16* (2006.01)

(52) U.S. Cl.
CPC ......... *A61B 17/1615* (2013.01); *A61B 17/1655* (2013.01)

(58) Field of Classification Search
CPC ................... A61B 17/1615; A61B 17/1655
USPC ................... 606/79, 80; 408/227, 230
See application file for complete search history.

(56) References Cited

U.S. PATENT DOCUMENTS 180,554 A * 8/1876 Cubberley ............ 408/230
1,309,706 A * 7/1919 Taylor ............ 408/230
(Continued)

FOREIGN PATENT DOCUMENTS

WO    WO 2011/113115 A1    9/2011

OTHER PUBLICATIONS

International Preliminary Report on Patentability re International Application No. PCT/AU2011/001539 dated May 24, 2012, in 13 pages.

(Continued)

*Primary Examiner* — Matthew Lawson
*Assistant Examiner* — Si Ming Lee
(74) *Attorney, Agent, or Firm* — Knobbe Martens Olson and Bear LLP

(57) ABSTRACT

A drill bit (1) has a central axis (A) and a tapered cutting end part (2) terminating in a drill tip (3) at one end of the drill bit (1), a shank (4) extending from an opposing end of the drill bit (1), and a body (4a) extending between the cutting end part (2) and the shank (4). A plurality of flutes (5) are formed in the drill bit (1) and helically extend along the body (4a) into the cutting end part (2). Each flute (5) has a flute leading side wall (6) and a flute trailing side wall (7). A land (9) is defined on the body (4a) between each of the flutes (5) and extends to the cutting end part (2). In any body cross-sectional plane extending perpendicular to the central axis (A) through the body (4a), a land leading edge region (11) of each land (9) adjoining the flute trailing side wall (7) of a leading adjacent flute (5) is convexly curved.

21 Claims, 15 Drawing Sheets

(56) References Cited

U.S. PATENT DOCUMENTS 2,404,048 A * 7/1946 Gepfert .................... 408/228
2,404,049 A * 7/1946 Gepfert .................... 408/230
4,561,813 A * 12/1985 Schneider ................ 408/230
4,659,264 A * 4/1987 Friedline .................. 408/204
4,975,003 A * 12/1990 Hosoi ....................... 408/230

OTHER PUBLICATIONS

International Search Report re International Application No. PCT/AU2011/001539 dated Jan. 18, 2012, in 3 pages.

* cited by examiner

DRILL BIT

TECHNICAL FIELD

The present invention relates to the field of drill bits and in particular relates to, but is not limited to, an orthopaedic drill bit.

BACKGROUND OF THE INVENTION

Drill bits are traditionally formed from a rod/shaft of high strength metallic material by grinding two or more helical gulleys, known as flutes, into the side wall of the rod extending from the operative front end of the rod towards the rear end, leaving a cylindrical shank at the rear end of the rod. The flutes are separated by lands that define the full diameter of the rod. To reduce the drag that would otherwise be experienced between the lands and the wall of the hole being drilled, the trailing region of each of the lands is ground, providing a slightly reduced diameter over this portion of the drill bit, known as a land relief. This leaves only a leading portion, known as a margin of the land, defining the full diameter of the drill. The leading edge of the margin defines a sharp secondary cutting edge with the trailing side wall of the adjacent flute, which is known as a cutting lip. During drilling operations, only the margin portion of the land engages the wall of the hole in the material being drilled, thereby reducing drag acting on the drill bit and, accordingly, reducing the likelihood of the drill bit binding.

The cutting end part of the drill bit is traditionally formed by grinding the end region of the rod to provide a generally conical end part, known as a point, with end or tip faces extending from each land towards either a chiselled edge, for designs with two flutes, or a sharp point tip for designs with three or more flutes. A primary cutting edge is defined by the junction between the leading edge of each of the tip faces and the adjacent trailing side wall of the adjacent flute. It is these primary cutting edges that cut material being drilled at the end of the drill hole. The shavings of swarf cut from the material pass along the flutes towards the rear of the drill bit, thereby creating room for more material to be cut or shaved and passed into and along the flutes for ejection from the rear end of the flutes.

In the body part of the drill bit, the margin forms an included angle with the trailing side wall of the adjacent flute. The smaller this included angle, the sharper the secondary cutting edge is. A sharper cutting edge has traditionally been desired to increase cutting efficiency. A sharper secondary cutting edge provides more aggressive engagement of the material being cut. If the included angle at the secondary cutting edge is too small, this can lead to decreased operator control, undesirably higher torque and uncontrollable cutting power.

When small included angles are provided at the secondary cutting edges, should the operator move the drill bit off-centre during the drilling process, the secondary cutting edges will have a tendency to widen the hole, as the relatively sharp secondary cutting edges will continue to cut and widen the drill hole. This will have an adverse effect on the security of any screw subsequently screwed into the drill hole. In orthopaedic applications this can lead to screw pullout and implant failure.

In orthopaedic applications, sharp secondary cutting edges can also result in potential damage to soft tissue such as tendons, ligaments, adjacent tissue and other vital organs. Flute designs in traditional drill bits tend to engage soft tissue, resulting in the tissue being wrapped around the drill bit, leading to considerable tissue trauma. This can lead to increased trauma to the patient and, possibly, in the case of arterial damage, can lead to death.

In an effort to avoid these problems, greater included angles are typically employed at the secondary cutting edges by controlling the design of the flute, and particularly the cross-sectional radius of the flute. The larger the radius of the flute, the greater the included angle at the cutting edge, resulting in a less aggressive secondary cutting edge. Larger radius flute cross-sections, however, have a tendency to produce a larger drill bit core diameter and decrease the amount of material in the drill bit towards the full overall diameter of the drill bit, thereby reducing the moment of inertia of the drill bit. This results in the drill bit being more prone to destructive failure when a bending or polar moment is applied to the drill bit. Providing a larger flute radius to soften the secondary cutting edge also results in the primary cutting edge, on the cutting end part, also becoming less aggressive, thereby reducing the cutting efficiency of the drill bit.

In orthopaedic applications, most drilling procedures require the drilling of the bone through the centre or hollow part of the bone known as the medullary canal. Drilling to fixate a fracture requires drilling from one side of cortex to the other. These cortices are known as the near cortex and far cortex. Beyond the far cortex lies soft tissues such as muscles, veins and arteries.

Also in some cases bone structures being drilled into generally comprise a hard, dense, thin external layer of compact or cortical bone and an inner layer of lighter, spongy or cancellous bone. The hardness and density of the cortical bone results in it being significantly tougher to drill through than the cancellous bone.

With typical orthopaedic drill bits, it is difficult to judge when the cutting end part is about to break through the cortical bone. This breakthrough occurs almost immediately after the drill bit has progressed through the bone to an extent where the rear end of the primary cutting edge (at the full diameter of the drill bit) first engages the bone surface, providing a hole in the bone surface that is the full diameter of the drill bit.

Once the drill bit breaks through the near cortex it travels through the hollow part of the bone into the far cortex where it breaks through into soft tissue. The soft tissue provides little or no resistance and the axial load applied to the drill bit by the operator, advancing the drill bit, can result in the breakthrough being sudden, with the drill bit rapidly overshooting deep into the muscles, veins and arteries beyond the required hole depth, potentially resulting in significant increased trauma and in some cases, where arterial damage may be caused, death.

Orthopaedic drill bits which have sharp secondary cutting edges may also cause difficulty when drill guides are used to accurately place the drill bit and drill a hole into bone tissue prior to accurate placement of a screw implant. This practice of utilising drill guides has become commonplace in modern orthopaedic surgery. The sharp secondary cutting edge of the drill bit tends to scratch and burr the inside of the guide, leading to potential for the drill bit to become jammed inside the drill guide. The burrs may also break free from the guide and enter the body of the patient. Jamming of a drill bit also prevents subsequent use of the guide after drill bit removal to deploy the implant screw down the guide for accurate bone fixation. The potential for scratching or burring of the guide is also enhanced where a land relief is ground into the trailing region of each land. This reduces the area over which the drill bit contacts the guide if any non-axial force is applied to the drill bit, such that the non-axial force is transferred by contact to the guide over a smaller area, and thus with greater pressure, increasing the chance of scratching or burring of the guide. Sharp, secondary cutting edges, also tear surgical gloves, which can lead to cross-contamination

OBJECT OF THE INVENTION

It is an object of the present invention to substantially overcome or at least ameliorate at least one of the above disadvantages.

SUMMARY OF THE INVENTION

In a first aspect the present invention provides a drill bit having a central axis and comprising:
a tapered cutting end part terminating in a drill tip at one end of said drill bit;
a shank extending from an opposing end of said drill bit;
a body extending between said cutting end part and said shank;
a plurality of flutes formed in said drill bit and generally helically extending along said body into said cutting end part, each said flute having a flute leading side wall and a flute trailing side wall;
a land defined on said body between each of said flutes and extending to said cutting end part;
wherein, in substantially any body cross-sectional plane extending perpendicular to said central axis through said body, a land leading edge region of each said land adjoining said flute trailing side wall of a leading adjacent said flute is convexly curved.

Typically in substantially any said body cross-sectional plane, each said land leading edge region has a radius of at least 0.20 mm Typically, in substantially any said body cross-sectional plane, each said land is leading edge region has a radius of at least 0.02 times an overall diameter of said drill bit.

More typically, in substantially any said body cross-sectional plane, each said land leading edge region has a radius of at least 0.04 times an overall diameter of said drill bit.

In at least one embodiment, each said land comprises:
said land leading edge region of said land;
a land margin adjoining said land leading edge region of said land;
a land relief extending from said margin toward a trailing adjacent said flute; and
a land transition region blending said land relief into said flute leading side wall of said trailing adjacent flute;
wherein, in any said body cross sectional plane, said land margin of each said land lies on a circle extending about said central axis and each said land leading edge region, each said land relief and each said transition region lies entirely within said circle.

Typically, in substantially any said body cross-sectional plane, said land relief is convexly curved.

Typically, in substantially any said body cross-sectional plane, said land relief is inclined with respect to said land margin toward said central axis.

Preferably, in substantially any said body cross-sectional plane, said land relief is inclined with respect to said land margin towards said central axis at an angle of 2 to 30 degrees, more preferably 5 to 15 degrees, at a junction therebetween.

Alternatively, in substantially any said body cross-sectional plane, said land relief curves inwardly from said land margin towards said central axis.

Typically, in substantially any said body cross-sectional plane, said land transition region is curved and smoothly blends said land relief into said flute leading side wall of said trailing adjacent flute.

In at least one form, in substantially any said body cross-sectional plane, said land transition region has a radius of at least 0.08 times an overall diameter of said drill bit.

In at least one form, in substantially any said body cross-sectional plane, said land transition region has a radius of at least 0.2 times an overall diameter of said drill bit.

Typically, said drill bit has three said flutes.

Typically, said drill bit is an orthopaedic drill bit.

In at least one preferred embodiment, said drill bit further comprises a plurality of tip faces defined on said cutting end part and extending from one of said lands to said is drill tip, said tip faces being separated by said flutes up to a forward end of each of said flutes, each said tip face defining a primary cutting edge with said flute trailing side wall of the leading adjacent said flute;
wherein each said primary cutting edge extends from one of said land leading edge regions, has a primary cutting edge transition region adjoining the respective said land leading edge region and, in substantially any transition region cross-sectional plane extending perpendicular to said central axis through said primary cutting edge transition region, said primary cutting edge is convexly curved and/or an adjoining radially outer region of said flute trailing side wall of the leading adjacent said flute is configured such that said primary cutting edge defines an increased included angle between said flute trailing side wall and the adjoining said tip face compared to a corresponding included angle in any cross-sectional plane forward of said primary cutting edge transition region.

In one form, each said primary cutting edge has a radius in said primary cutting edge transition region, measured in a said transition region cross-sectional plane that increases towards the respective said land leading edge region, blending said primary cutting edge from a forward, sharp region of said primary cutting edge into said land leading edge region.

In one form, each said primary cutting edge defines an included angle between said flute trailing side wall and the adjoining said tip face, measured in a said transition region cross-sectional plane that increases towards the respective said land leading edge region.

Typically for each said primary cutting edge, in a cross-sectional plane extending through an intersection between each said primary cutting edge and the respective said land leading edge region, said primary cutting edge has a radius substantially equal to a radius of said land leading edge region. Typically, said radius is at least 0.20 mm.

In at least one embodiment, each of said flutes extends to adjacent said drill tip and each said primary cutting edge extends from one of said land leading edge regions in a variable conic helix type manner with a primary cutting edge helix angle that decreases from substantially equal to a helix angle of the respective said land leading edge region, at said land leading edge region, towards zero as it approaches said drill tip.

In the context of the present specification, a variable conic helix is defined as a three-dimensional curve that has the general form of a conic helix except that the helix angle, defined between a tangent to the curve at any point and the central axis of the curve, is not constant as with a regular helix, but varies.

In one form, each said land comprises:
said land leading edge region of said land;
a land margin adjoining said land leading edge region;

a land transition region blending said land margin into said flute leading side wall of said trailing adjacent flute;

wherein, in substantially any said body cross-sectional plane, said land margin of each said land lies in a circle extending about said central axis and said land margin extends across at least a majority of a width of said land.

In one form, said body is provided with a thread extending from adjacent said cutting end part towards said shank, said thread being defined on said land margins.

In substantially any said body cross-sectional plane, said convexly curved land leading edge region may be defined by a plurality of discrete chamfered surfaces.

BRIEF DESCRIPTION OF THE DRAWINGS

Preferred embodiments of the present invention will now be described, by way of example only, with reference to the accompanying drawings wherein.

DETAILED DESCRIPTION OF THE PREFERRED EMBODIMENTS

Figure 1:
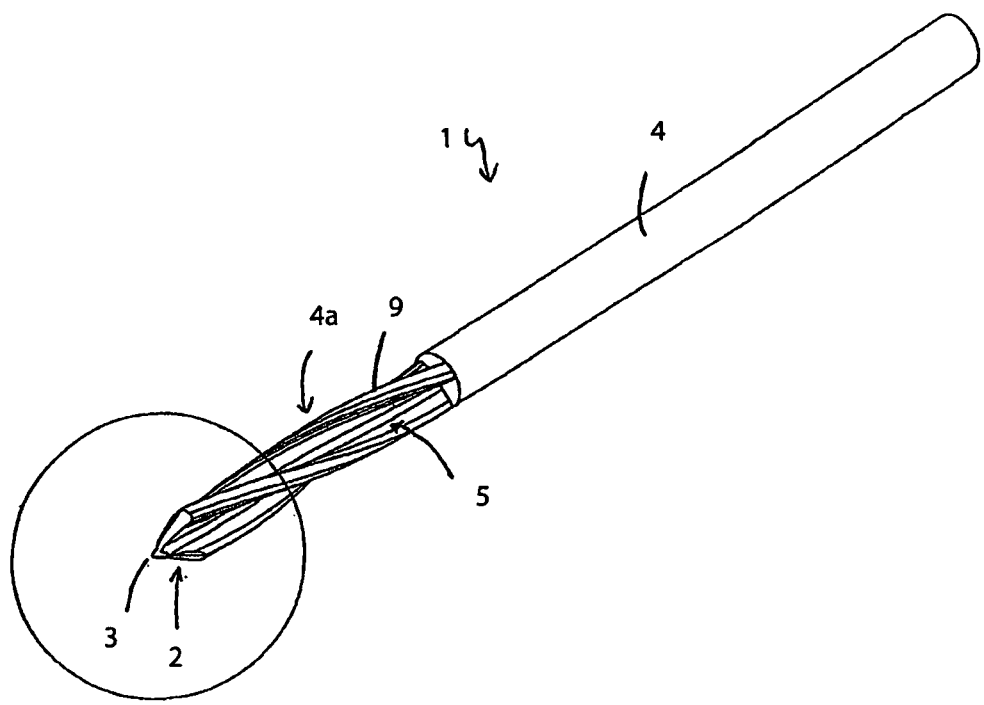
FIG. 1 is a perspective view of a drill bit according to a first embodiment.

Referring to FIGS. 1 to 3e of the accompanying drawings, a drill bit 1 according to a first embodiment has a tapered cutting end part 2 terminating in a drill tip 3 at a front, operative end of the drill bit 1, with a shank 4 extending from an opposing rear end of the drill bit 1. The shank 4 is configured to be received within the chuck of a drill in the usual way, and will typically be cylindrical although it may be hexagonal in cross-section or any other suitable shape. A body 4a of the drill bit 1 extends between the cutting end part 2 and the shank 4. A plurality of flutes 5 are formed in the drill bit 1. In the embodiment depicted there are three flutes 5 that each helically extend along the body 4a from adjacent the shank 4 into the cutting end part 2, although it is envisaged that the drill bit 1 may have only two flutes 5 or four or more flutes 5. Each of the flutes 5 extends into the cutting end part 2 towards the drill tip 3, but finishes just short of the drill tip 3 as a result of the tapering of the cutting end part 2.

In the embodiment depicted, the drill bit 1 is configured to be rotated in a clockwise direction when viewed from the rear of the drill bit 1. Throughout this specification, various features of the drill bit will be referred to as "leading" or "trailing", with this terminology indicating features that lead or trail respectively as the drill bit rotates in the intended manner. Each of the flutes 5 has a flute leading side wall 6 (which faces against the intended direction of rotation) and a flute trailing side wall 7 (which faces in the intended direction of rotation). The flute leading side wall 6 is joined to the flute trailing side wall 7 by way of a flute base 8 located therebetween. As best depicted in the cross-sectional views of FIGS. 3a through 3d, the flute leading side wall 6, flute base 8 and flute trailing side wall 7 effectively form a smooth continuous surface. The flutes 5 are each formed with a helix angle of about 13 degrees in the embodiment depicted, although the helix angle may be adjusted as desired for different applications. Typical helix angles will be between 10 degrees and 45 degrees. The helix of the flutes 5 is configured such that the rear end of each flute 5 trails the front end as the drill bit 1 rotates in the intended direction. The flute bases 8 have a slight taper of about 1 degree with respect to the central axis A of the drill bit, reducing the depth of the flutes 5 towards the shank 4. Typical taper angles will be between 0 degree and 3 degrees.

A land 9 is defined between each of the flutes 5. As best depicted in the cross-sectional view of FIG. 3a, each land 9 has a land leading edge region 11 adjoining the adjacent flute trailing side wall 7 of the adjacent flute 5 directly leading the land 9. A land margin 10 is defined adjoining and trailing the land leading edge region 11. Each land 9 also has a land relief 12 which extends from the land margin 10 towards the adjacent flute leading side wall 6 of the flute 5 directly trailing the land 9.

Figure 3:
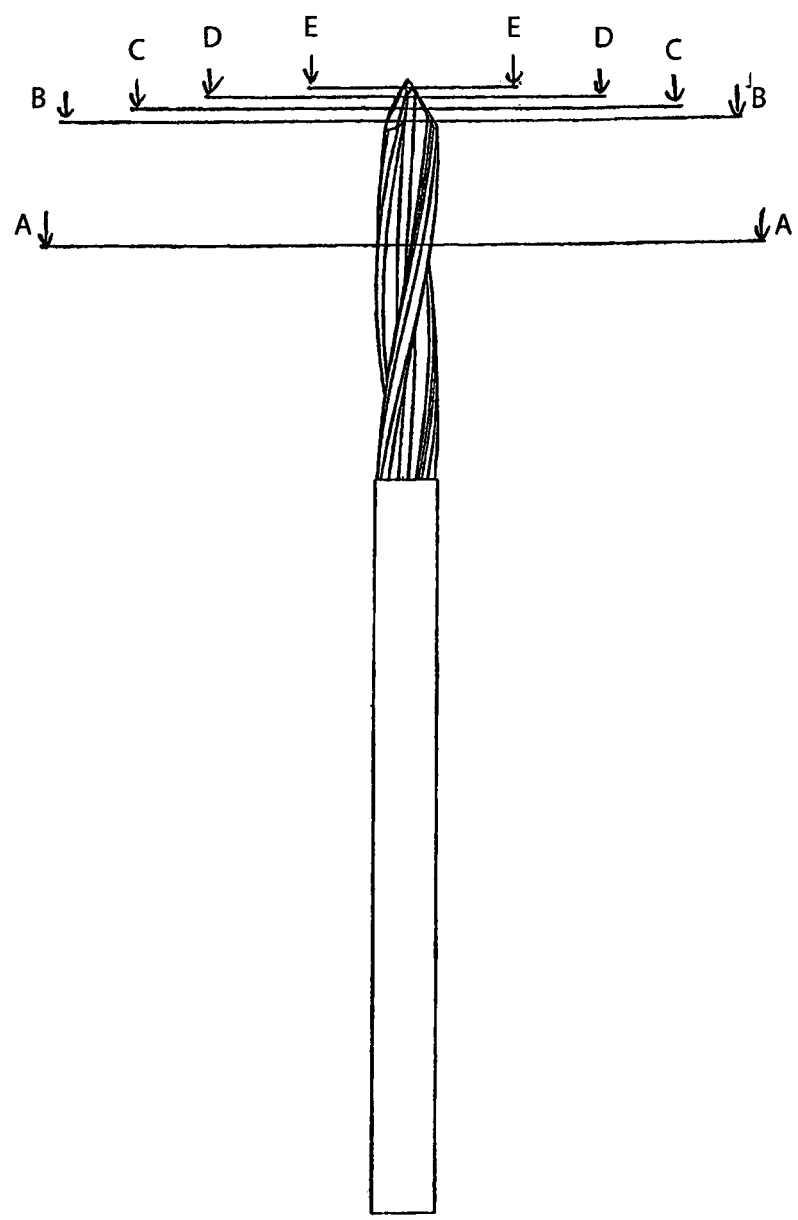
FIG. 3 is a front elevation view of the drill bit of FIG. 1.
Figure 3A:
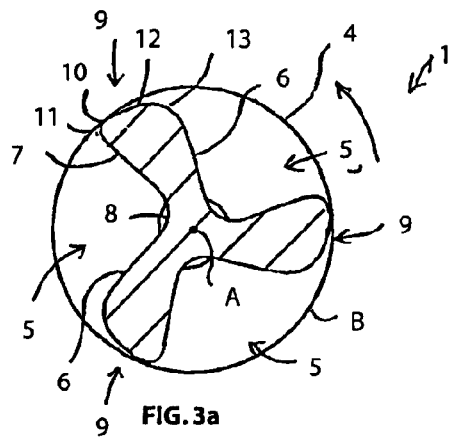
FIGS. 3a through 3e are each cross-sectional views of the drill bit of FIG. 1 taken at sections A-A to E-E of FIG. 3 respectively.

The land leading edge region 11 of each land 9 is convexly curved when viewed in at least substantially any cross-sectional plane extending perpendicular to the central axis A of the drill bit through the body 4a (here referred to as a body cross-sectional plane, such as the cross-sectional plane depicted in FIG. 3a). This may be contrasted to typical prior art drill bits that define a sharp cutting edge at the intersection between the leading edge of each land and the adjacent flute trailing side wall. As a result, the body 4a of the drill bit 1 is not provided with any secondary cutting edge, as is the case with typical known drill bits, leaving the entire cutting operation to the cutting end part 2, as will be described in further detail below. As a result, in the event that the operator moves the drill bit off-centre during the drilling process, there will be less tendency for the drill hole to be cut and widened by the misaligned body of the drill bit as compared to where sharp secondary cutting edges are provided on the body. There is also a reduced possibility of damage to soft tissue in orthopaedic applications, reducing the possibility of the body of the drill bit biting into soft tissue and having soft tissue engaged and wrapped around the body. Providing a convexly curved land leading edge region on each land also improves the smoothness of operation of the drill bit, reducing the aggressiveness of engagement of the drill bit, enabling provision of a smooth cutting process under decreased torque. These benefits may also be achieved without adversely affecting the structural integrity of the drill bit, maintaining a significant moment of inertia of the drill bit by not needing to reduce the amount of material in the body of the drill bit at full diameter to accommodate a greater angle between the flute trailing face and land to soften a secondary cutting edge. The convex curvature of the land leading edge region 11 may be achieved with a plurality of discrete chamfered surfaces rather than a continuous curve.

For each land, the land leading edge region 11 will typically have an average radius of at least 0.2 mm. In particular, for a typical orthopaedic drill bit having an overall diameter of 4.5 mm, the land leading edge regions will typically have a constant radius of at least 0.2 mm measured in at least substantially any body cross-sectional plane extending perpendicular to the central axis A through the body 4a. In the particular arrangement depicted, the radius of the land leading edge region 11 is approximately 0.3 mm. The radius of the land leading edge region may vary in any cross-sectional plane (that is, the land leading edge region 11 need not be formed as a constant radius arc). In at least substantially any body cross-sectional plane perpendicular to the central axis A extending through the body 4a, the average radius of each land leading edge region 11 would typically be at least 0.02 times the overall diameter of the drill bit, more particularly at least 0.04 times the overall diameter of the drill bit.

In the particular arrangement depicted, a land transition region 13 blends the land relief 12 into the flute leading side wall 6, as best depicted in FIG. 3a. This may be contrasted with a typical prior art drill bit wherein the land relief and flute leading side wall meet at a sharp edge (although it is envisaged that the curved land leading edge region described above may be used in conjunction with a conventional land relief/flute leading side wall). The transition region 13 will typically be curved so as to smoothly blend the land relief 12 into the flute leading side wall 6. The land transition region 13 will preferably have a radius, when measured in a body cross-sectional plane perpendicular to the central axis A of the drill bit (such as the cross-sectional planes depicted in FIGS. 3a through 3e) which may vary within the range of 0.08 to 0.3 times the overall diameter of the drill bit 1, or between 0.2 and 0.3 times the overall diameter. In the specific embodiment depicted, the drill bit 1 has an overall diameter of 4.5 mm, and the land transition region 13 has a radius which varies between approximately 1.08 mm adjacent the land relief 6 and 0.4 mm adjacent the flute leading side wall 6. Rather than being curved, the land transition regions 13 could each be defined by one, or preferably two or more, chamfered surfaces.

The land margin 10 constitutes a part cylindrical portion of the land 9 which is not ground away from the cylindrical shaft from which the drill bit 1 is formed. The land margin 10 has a width (measured in a body cross-sectional plane) of about 0.2 mm in the embodiment depicted, however, it is envisaged that the land margin 10 may have a minimal width, effectively defined by the intersection of the land leading edge region 11 and the land relief 12. The land margins 10 each lie on a circle B extending about the central axis A and having a diameter equal to the overall diameter of the drill bit (being equal to the diameter of the shank 4 in the embodiment depicted). The land leading edge region 11, land relief 12 and land transition region 13 of each land are ground away from the cylindrical shaft from which the drill bit 1 is formed. Accordingly, at any body cross-sectional plane extending perpendicular to the central axis A through the lands 9, each land leading edge region 11, land relief 12 and land transition region 13 lies entirely within the circle B as depicted in FIG. 3a. The land relief 12 is convexly curved and is typically inclined with respect to the land margin 10 towards the central axis A, defining an edge between the land margin 10 and the land relief 12. Alternatively, the land relief 12 may gradually curve inwardly from the land margin 10 towards the central axis A without leaving any definite edge therebetween. In the embodiment depicted, the land relief 12 is inclined with respect to the land margin 10, when measured in a body cross-sectional plane, by about 11 degrees at the junction therebetween. Typical inclination angles will be between 5 degrees and 25 degrees. As such, the land relief 12 provides a greater area between its surface and the circle B than typical prior art designs, which are generally part cylindrical with a diameter only slightly less than the overall diameter of the drill bit.

The land relief 12 provides a clearance between the bulk of the land 9 and the wall of the hole being drilled, thereby further reducing drill bit drag. As stated above, this clearance is generally greater than that provided with typical prior art designs, particularly towards the land transition region 13. This increased clearance, together with the additional clearance provided by the land transition region 13, provides an additional, secondary flow path for swarf to pass along the drill bit 1 as the flutes 5 begin to fill and increase pressure. The land transition region 13 also provides an opportunity for swarf material that is not immediately passed into the flutes 5, but has travelled into the land relief 12, to flow into the flutes 5. The land transition region 13 is believed to create a region of reduced pressure which actively draws swarf from the land relief 12 into the adjacent flute 5. Efficiency of the drill bit 1 is thus not affected by a build-up of swarf material caught within the land relief region 12.

Each of the flutes 5 and adjacent land leading edge region 11, land transition region 13 and land relief 12 may be formed by grinding the shaft from which the drill bit 1 is formed in a single grinding operation with a single shaped grinding wheel.

The tapered cutting end part 2 may be of a conventional configuration. Alternatively, the cutting end part 2 may advantageously be of either of the specific forms depicted in the accompanying drawings.

Figure 2:
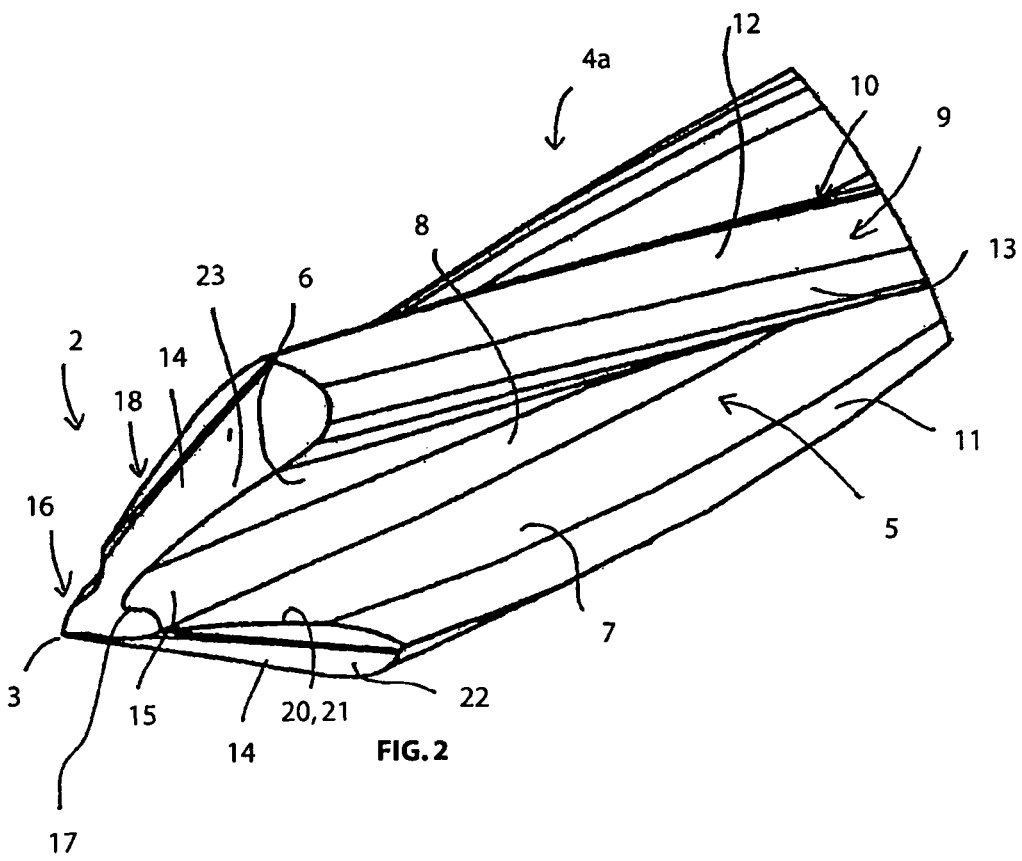
FIG. 2 is an enlarged perspective view of the cutting end part of the drill bit of FIG. 1.

Referring specifically to FIG. 2, the tapered cutting end part 2 of the drill bit 1, comprises three tip faces 14, one corresponding to each of the lands 9. Each tip face 14 extends from the corresponding land 9 to the drill tip 3 and effectively constitutes a tapered end of the corresponding land 9. The tip faces 14 define an included drill point angle, which is about 60° in the embodiment depicted, although the drill point angle may be altered as desired to suit the material to be drilled. Drill point angles of between 40° and 80° would be typical. The flutes 5 extend between the tip faces 14 until they terminate where the tapered cutting end part 2 is tapered down to the thickness of the central web 15 that separates the flute bases 8.

Each tip face 14 is separated into two regions. A first tip face region 16 extends from adjacent the end 17 of each of the flutes 5 to the drill tip point 3. This first tip face region 16 constitutes the solid forward end of the cutting end part 2 where each of the tip faces 14 meets without a flute 5 therebetween. The second tip face region 18 constitutes the region extending from the first tip face region 16 to the forward end of the adjacent land 9. The second tip face regions 18 are each separated by one of the flutes 5.

Figure 3B:
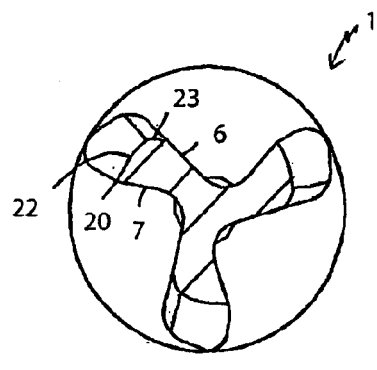
Figure 3C:
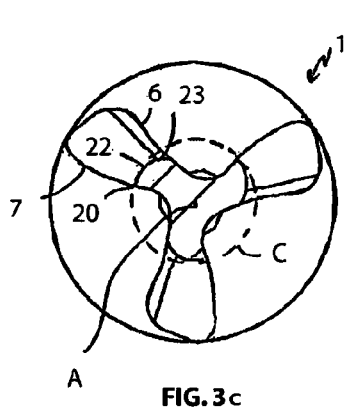
Figure 3D:
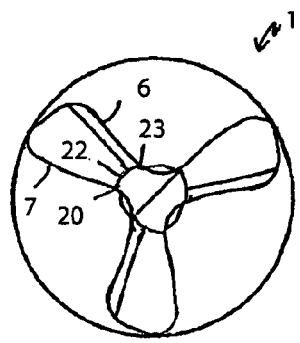

Each of the second tip face regions 18 has a similar configuration to that of each of the lands 9. This configuration is best appreciated from each of the cross-sectional views of FIGS. 3b through 3d, representing successive cross-sectional planes taken through the second tip face regions 18. Each second tip face region 18 has a leading face margin 20 which defines a primary cutting edge 21 with the adjacent flute trailing side wall 7 of the adjacent flute 5 directly leading the second tip face region 18. In the absence of a secondary cutting edge in the body 4a of the drill bit 1, the primary cutting edges 21 perform substantially the entire cutting function of the drill bit 1 (along with the tertiary cutting edges 75 described below). Providing convexly curved land leading edge regions 11 in place of secondary cutting edges allows the primary cutting edges 21 to be kept sharp by using a small radius grinding wheel to form the flutes 5 along their length, keeping a relatively small included angle between the flute trailing side wall 7 and the face margin 20. An aggressive cut may still be provided by the primary cutting edges 21, maintaining an efficient and smooth cutting process.

A face relief 22 extends from the face margin 20 towards the adjacent flute leading side wall 6 of the flute 5 directly trailing the second tip face region 18. In the embodiment depicted, the face margin 20 is effectively represented by a thin line defined by the primary cutting edge 21, rather than a more substantial margin as is the case with the land margin 10, with the face relief 22 smoothly blending into the face margin 20. A face transition region 23 blends the face relief 22 into the flute leading side wall 6. This can again be contrasted with a typical prior art drill bit where the tip face typically meets the flute leading side wall at a sharp edge.

Referring to FIG. 3c, the face margins 20 each lie on a circle C extending about the central axis A, and having a diameter that is reduced as compared to the overall diameter of the drill bit, given the tapering of the tapered cutting end part 2. The face relief 22 and face transition region 23 are ground away from the basic tapered form of the cutting end part 2. Accordingly, at any cross-sectional plane extending perpendicular to the central axis A through the second tip face regions 18, each face relief 22 and face transition region 23 lies entirely within the circle C as depicted in FIG. 3c.

In a similar manner to the land relief 12, the face relief 22 reduces drag on the drill bit 1. The configuration of the face transition region 23, blending the face relief 22 into the adjacent flute leading side wall 6 also enhances the flow of excess swarf, which is initially passed into an area adjacent the face relief 22 rather than directly into the flute 5, in a similar manner to that discussed above in relation to the land transition region 13.

Figure 3E:
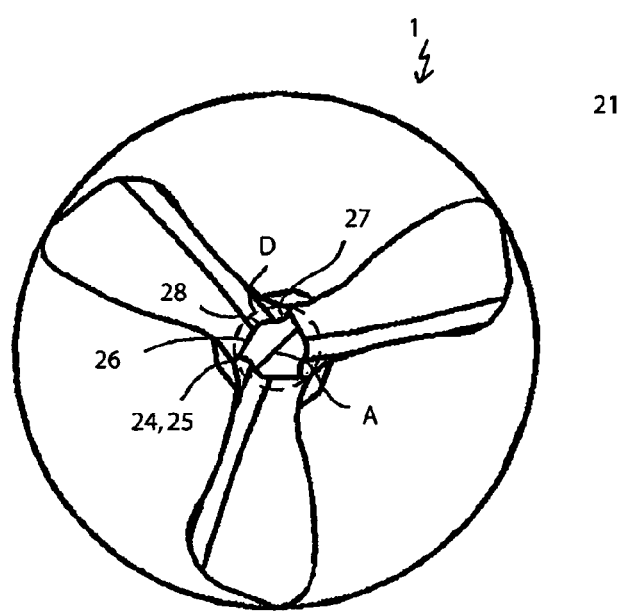
Figure 4:
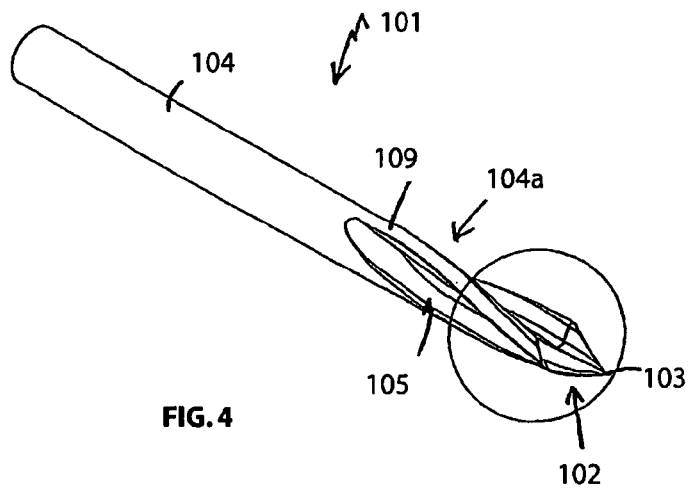
FIG. 4 is a perspective view of a drill bit according to a second embodiment.

Referring to FIGS. 2 and 3e, the first drill face region 16 also shares some aspects of the configuration of both the lands 9 and the second tip face regions 18. Each first tip face region 16 has a leading tip margin 24 defining a tertiary cutting edge 25 with the trailing edge of the adjacent first tip face region 16. As with the face margins 20, the tip margins 24 will typically be defined by a line constituting the tertiary cutting edge 25. The tip margins 24 may, however, have a broader width. A tip relief 26 extends from the tip margin 24 towards the adjacent trailing first tip face region. A gulley 27 is formed in each first tip face region 16 between the tip relief 26 and the leading edge of the directly trailing first tip face region. A curved tip transition region 28 blends each tip relief 26 into the adjacent gulley 27. The tip transition regions 28 each represent a continuation of a face transition region 23. Each of the gulleys 27 communicates with the end of an adjacent flute 5 and extends towards the drill tip 3 although it is envisaged that, in most applications, the gulley will not extend all the way to the drill tip 3 as can be seen in FIGS. 2 and 4. This is largely due to limitations in creating the gulleys 27 in such a fine region at the drill tip 3.

The tip margins 24 each lie on a circle D extending about the central axis A as depicted in FIG. 3e. Each tip relief 26, tip transition region 28 and gulley 27 lies entirely within the circle D.

The tip reliefs 26 again function in a similar manner to both the land reliefs 12 and face reliefs 22, both reducing drag and providing space for the passage of swarf. The gulleys 27 each provide a flow path for swarf from adjacent the drill tip 3 for feeding the swarf into the flutes 5. This may be contrasted with typical prior art drill bits, where the solid end portion of the cutting end part is substantially pyramid shaped without provision of any flow path for the passage of swarf. The arrangement of the gulleys 27 adjacent the tertiary cutting edges 25 also provides for much stronger tertiary cutting edges 25 than is the case for pyramid shaped end part designs.

FIGS. 4 to 10 of the accompanying drawings depict a drill bit 101 according to a second embodiment. Features of the drill bit 101 of the second embodiment that are identical or equivalent to features of the drill bit 1 of the first embodiment described above are generally identified reference numerals to those corresponding of the first embodiment, increased by 100.

The drill bit 101 has a tapered cutting end part 102 terminating in a drill tip 103 at a front, operative end of the drill bit 101, with a shank 104 extending from an opposing rear end of the drill bit 101. The shank 104 is configured to be received within the chuck of a drill. A body 104a of the drill bit 101 extends between the cutting end part 102 and the shank 104. A plurality of flutes 105 are formed in the drill bit 101. In the second embodiment depicted there are three flutes 105 that each generally helically extend along the body 104a from adjacent the shank 104 into the cutting end part 102. In this embodiment, each of the flutes 105 extends into the cutting end part 102 to adjacent the drill tip 103. Each of the flutes 105 comprises a flute body region 105b extending along the body 104a, and a flute end region 105a extending along the cutting end part 102 from the junction between the cutting end part 102 and body 104a to adjacent the drill tip 103.

A land 109 is defined on the body 104a between each of the flutes 105. As best depicted in the cross-sectional view of FIG. 6a, each land 109 has a land leading edge region 111 adjoining the adjacent flute trailing side wall 107 of the adjacent flute 105 directly leading the land 109. A land margin 110 is defined adjoining and trailing the leading edge region 111. Each land 109 also has a land relief 112 which extends from the land margin 110 towards the adjacent flute leading side wall 106 of the flute 105 directly trailing the land 109.

Figure 5:
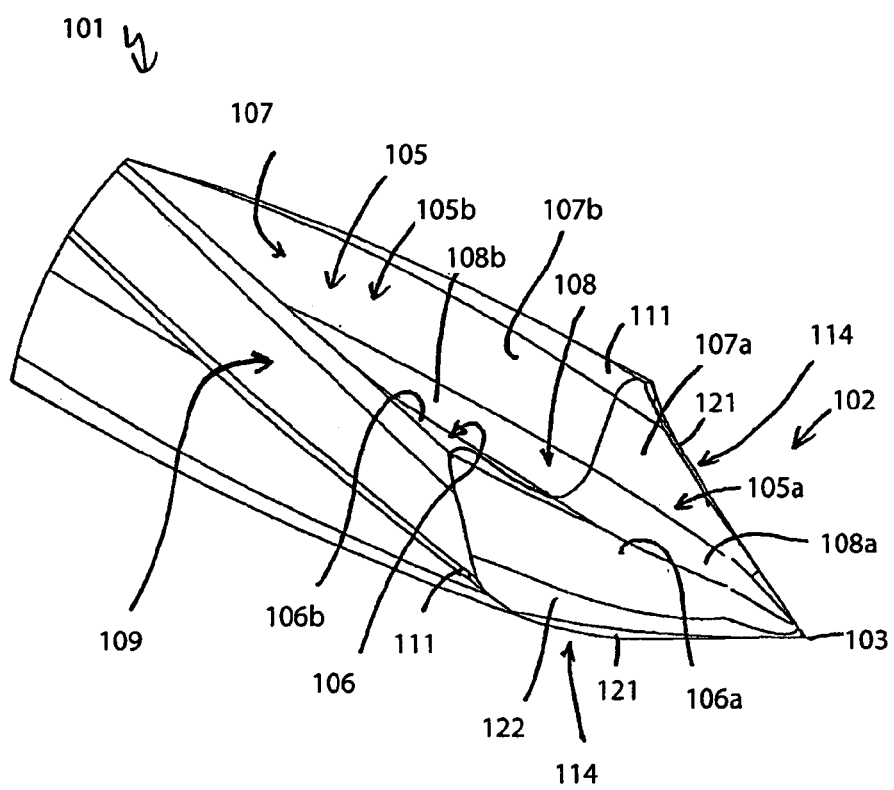
FIG. 5 is an enlarged perspective view of the cutting end part of the drill bit of FIG. 4.

Referring specifically to FIG. 5, the tapered cutting end part 102 of the drill bit 101 comprises three tip faces 114, one corresponding to each of the lands 109. Each tip face 114 extends from the corresponding land 109 to the drill tip 103 and effectively constitutes a tapered end of the corresponding land 109. The tip faces 114 define an included drill point angle, which is about 60 degrees in the embodiment depicted, although again the drill point angle may be altered as desired to suit the material to be drilled. The tip faces 114 are separated by the flutes 105 (in particular the flute leading regions 105a) up to adjacent the drill tip 103, at the end of the flutes 105.

In the second embodiment depicted, the drill bit 101 is again configured to be rotated in a clockwise direction when viewed from the rear of the drill bit 101. As described above, each of the flutes 105 has a flute leading side wall 106 and a flute trailing side wall 107. The flute leading side wall 106 is joined to the flute trailing side wall 107 by way of a flute base 108 located therebetween. As best depicted in the cross-sectional views of FIGS. 6a through 6e, the flute leading side wall 106, flute base 108 and flute trailing side wall 107 effectively form a smooth continuous surface. The flute leading side wall 106, flute trailing side wall 107 and flute base 108 may be divided into end and body regions, in the same manner as each flute 105 has been divided into a flute end region 105a and flute body region 105b, and numbered accordingly. That is, the flute leading side wall 106 may be divided into a flute leading side wall end region 106a and flute leading side wall body region 106b, the flute trailing side wall 107 may be divided into a flute trailing side wall end region 107a and flute trailing side wall body region 107b and the flute base may be divided into a flute base end region 108a and flute base body region 108b.

The flute body regions 105b are each formed with a constant helix angle of about 13 degrees in the embodiment depicted, although the helix angle may again be adjusted as desired for different applications. The land leading edge regions 111 are formed with the same constant helix angle. The helix of each of the flutes 105 is configured such that the rear end of each flute 105 trails the front end as the drill bit 101 rotates in the intended direction. The flute base body regions 108b have a slight taper of about 1 degree with respect to the central axis A of the drill bit, reducing the depth of the flute body regions 105b towards the shank 104. The flute base end regions 108a have a larger taper with respect to the central axis A of the drill bit such that the area of the transverse cross-section of the web defined between the flute base end regions 108a reduces towards the drill tip 103 thereby allowing the flute end regions 105a to extend to adjacent the drill tip 103. The flutes 105 would otherwise terminate at a greater distance from the drill tip 103 as a result of the taper of the cutting end part 102. Typically, the flute end regions 105a extend to within 0.1 mm of the drill tip 103 (equating to within about 0.02 times the diameter of a 4.5 mm diameter drill bit), or more typically within about 0.05 mm (0.01 times the drill bit diameter). In the particular embodiment depicted, the flute end regions 105a extend to within about 0.04 mm of the drill tip 103.

As best depicted in the various cross-sectional views of FIGS. 6b to 6e, each tip face 114 defines a primary cutting edge 121 with the flute trailing side wall end region 107a of the adjacent flute 105 that is directly leading the tip face 114.

In the second embodiment depicted, each flute end region 105a is formed to provide a primary cutting edge 121 that extends from the corresponding land leading edge region 111, at the intersection between the body 104a and cutting end part 102, in a variable conic helix type manner with a primary cutting edge helix angle that decreases from substantially equal to the land leading edge region helix angle at the land leading edge region 111, toward zero degrees as it approaches the drill tip 103. As noted above, in the context of the present specification, a variable conic helix is defined as a three-dimensional curve that has the general form of a conic helix except that the helix angle, defined between a tangent to the curve (here the primary cutting edge 121) and the central axis of the curve (here the central axis A), is not constant as with a regular helix, but varies. Accordingly, the primary cutting edge 121 gradually "straightens up" towards aligning with the central axis A as is perhaps most apparent in FIG. 4 which shows the primary cutting edge helix angle of each primary cutting edge 121 decreasing to zero degrees adjacent to the drill tip 103 such that, when viewed from the drill tip end of the drill bit 101, the primary cutting edges 121 initially extend radially from adjacent the drill tip 103. As is perhaps best depicted in FIG. 8, in the particular embodiment depicted, each primary cutting edge 121 extends at least substantially tangentially from the corresponding land leading edge region 111 when viewed in a plane extending tangentially through the land leading edge region 111 at the junction between the primary cutting edge 121 and the land leading region 111 and extending perpendicular to the central axis A. As a result, the flute end region 105a and flute body region 105b merge smoothly, particularly along the flute trailing side wall 107 and from the primary cutting edge 121 to the land leading edge region 111.

Figure 6:
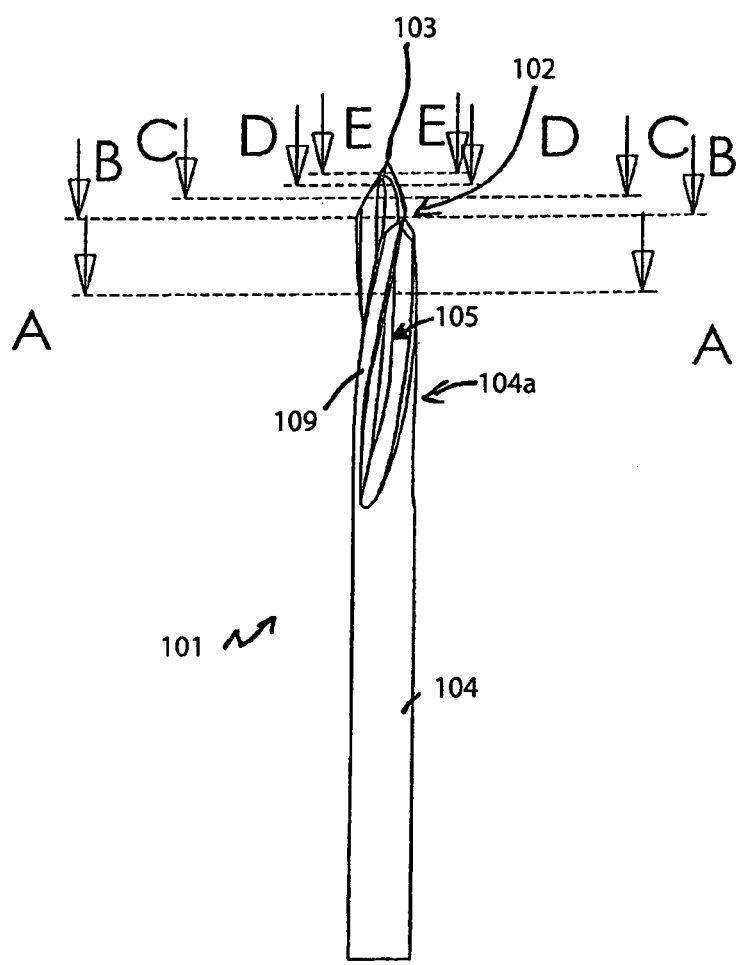
FIG. 6 is a front elevation view of the drill bit of FIG. 4.
Figure 6A:
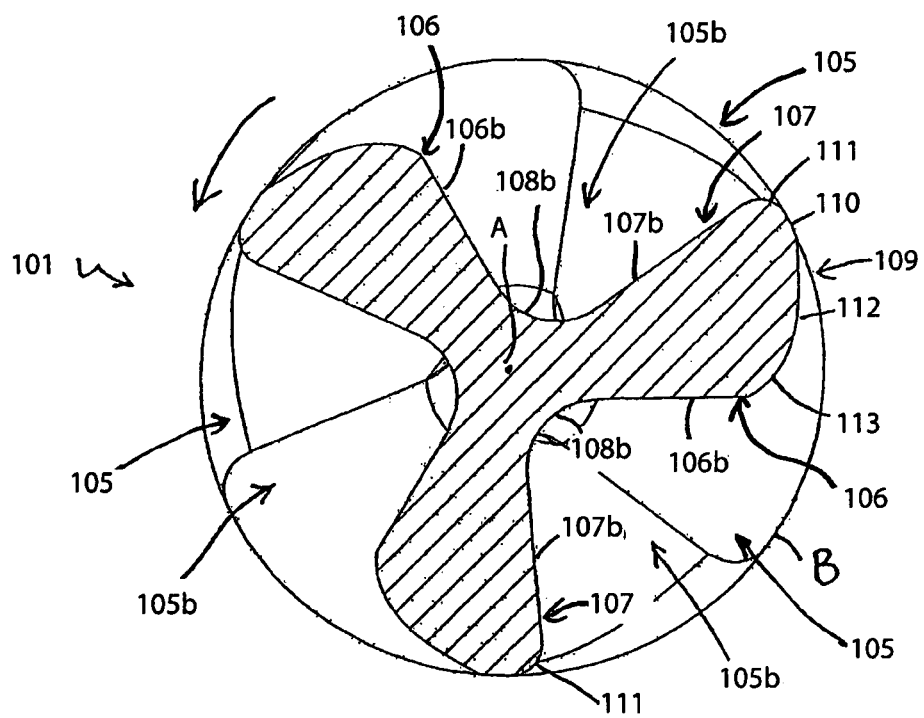
FIGS. 6a through 6e are each cross-sectional views of the drill bit of FIG. 4 taken at sections A-A to E-E of FIG. 6 respectively.
Figure 6B:
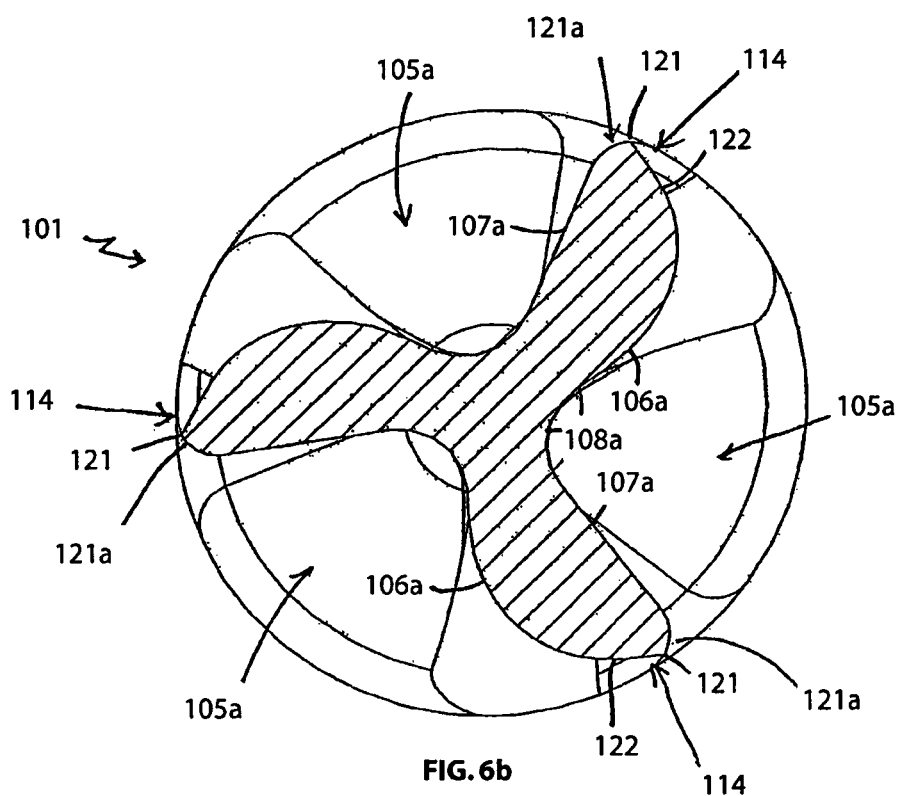
Figure 10:
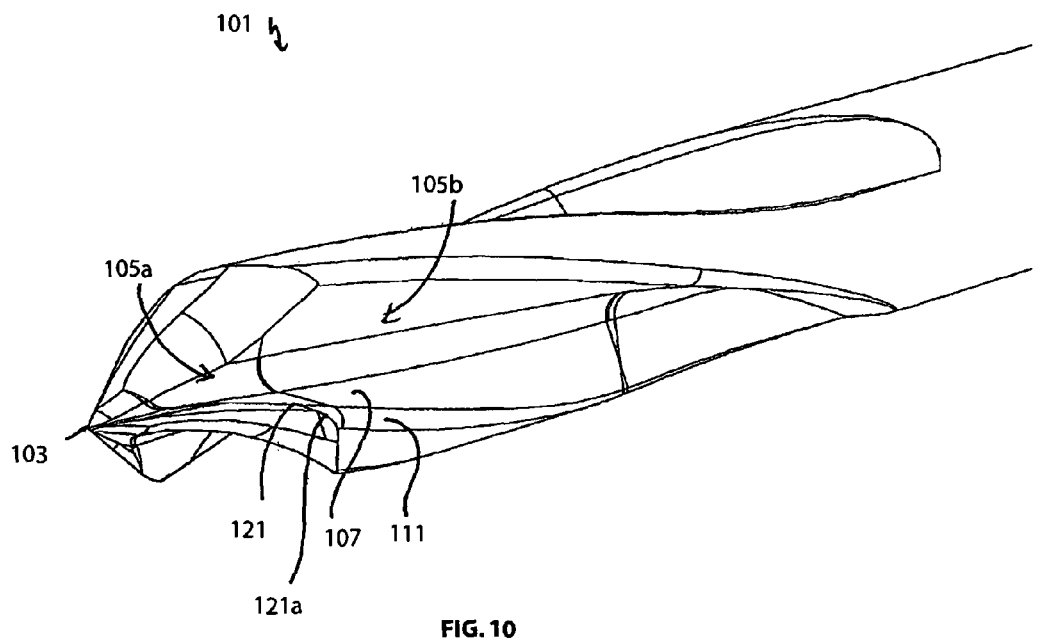

As best depicted in FIGS. 6b and 10, each primary cutting edge 121 has a primary cutting edge transition region 121a extending forward partway along the primary cutting edge 121 from the intersection with the land leading edge region 111. In the primary cutting edge transition region 121a, the primary cutting edge 121 is convexly curved, with the radius of the primary cutting edge 121, taken in a cross-sectional plane extending perpendicular to the central axis A, increasing to blend the forward, sharp region of the primary cutting edge into the land leading edge region 111 which, as discussed below, is convexly curved. In the primary cutting edge transition region 121a, the primary cutting edge 121 will typically have a radius, measured in the cross-sectional plane, that increases from zero at the forward end of the primary cutting edge transition region 121a to a radius equal to that of the land leading edge region 111 (discussed further below), which will typically be at least 0.2 mm, typically between 0.2 mm and 0.5 mm, and here is about 0.3 mm As is apparent from FIG. 6b, the convex curvature applied to the primary cutting edge 121 in the primary cutting edge transition region 121a might be construed as being applied to the adjacent radially outer region of the flute trailing side wall 107a of the leading adjacent flute 105, rather than being applied to the primary cutting edge 121 itself. With a configuration either applied or construed in such manner, the convex curvature of the adjoining radially outer region of the flute trailing side wall 107a results in the primary cutting edge 121 defining an increased included angle between the flute trailing side wall 121 and the adjoining tip face 114 equally results in a significantly less aggressive primary cutting edge 121 in the primary cutting edge transition region 121a. An equivalent effect could be achieved by, for example, providing a chamfer in the radially outer region of the flute trailing side wall 107a at the primary cutting edge 121 in the primary cutting edge transition region121a, rather than providing a convexly curved configuration. With such configurations, the included angle defined between the flute trailing side wall 107a and adjoining tip face 114 will typically increase towards the adjacent land leading edge region 111, thereby reducing the aggressiveness of the primary cutting edge 121 as it approaches full diameter where it adjoins the land leading edge region 111.

Figure 7:
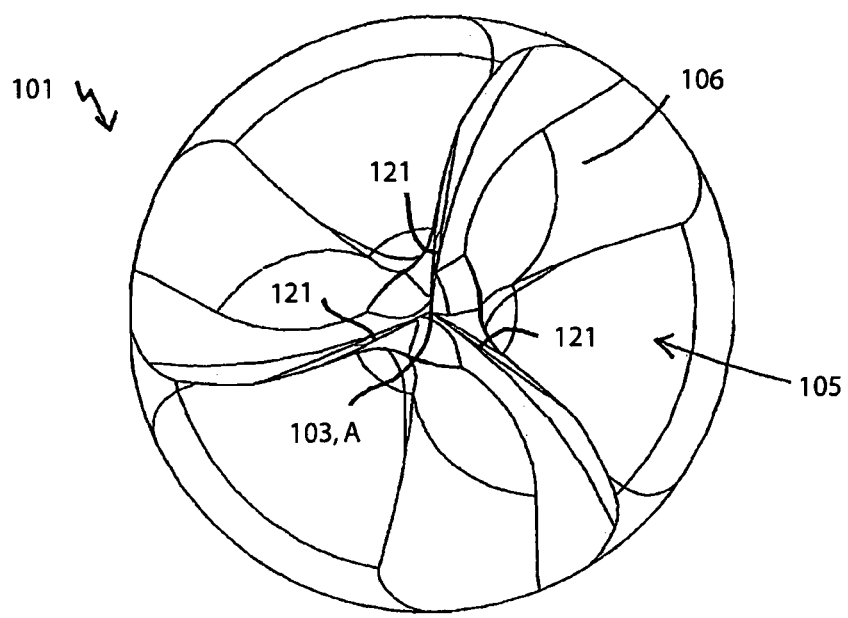
FIG. 7 is an end elevation view of the drill bit of FIG. 4.
Figure 8:
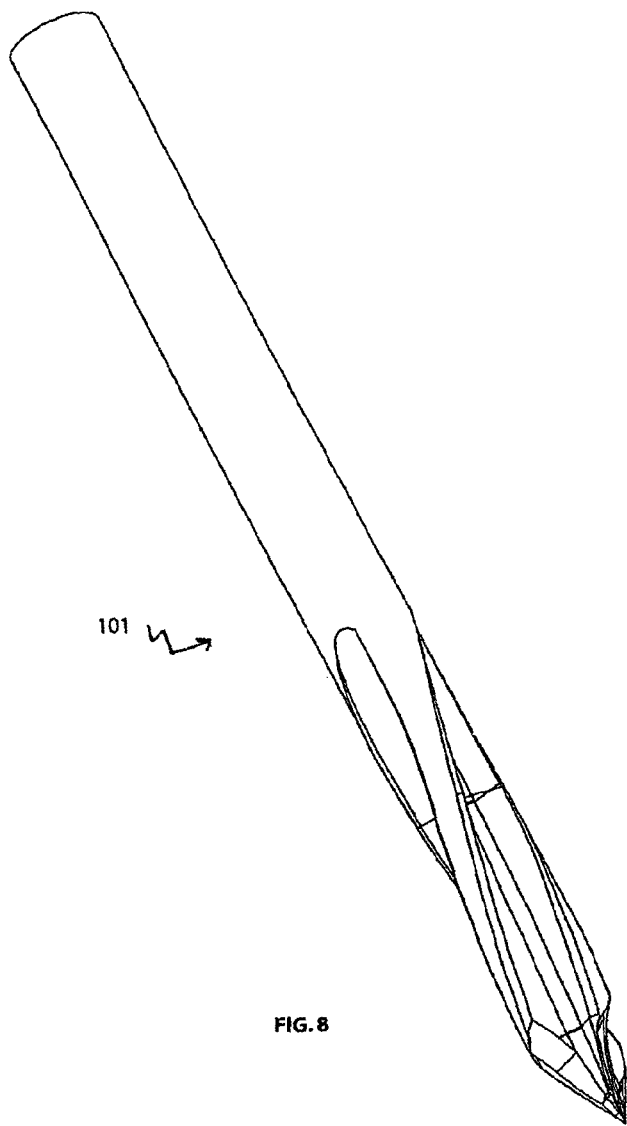
FIGS. 8 through 10 are each perspective/fragmentary perspective views of the drill bit of FIG. 4 as viewed from various angles.
Figure 9:
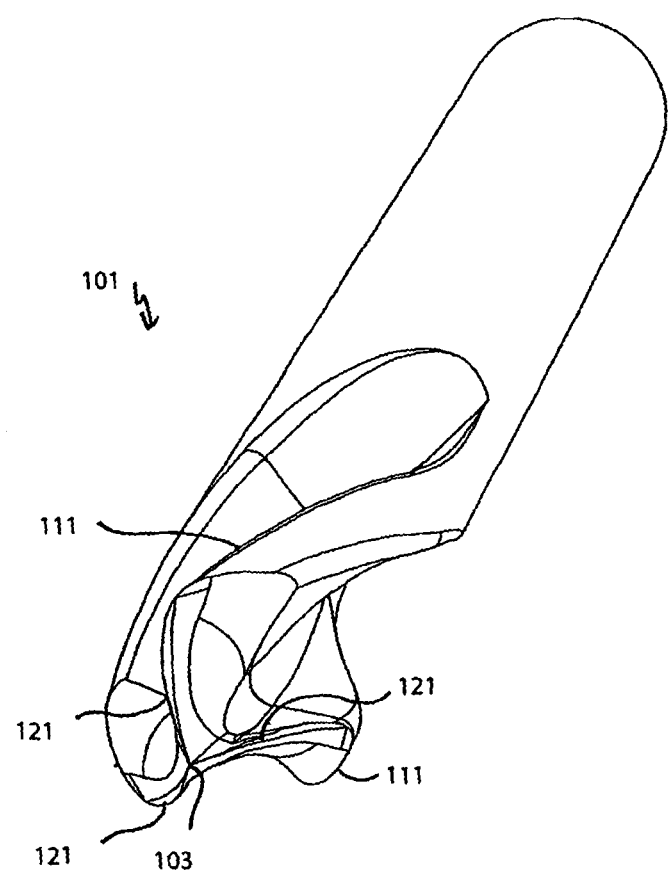

Typical prior art drills have a straight primary cutting edge and/or a primary cutting edge that ends well short of the drill tip. In such configurations, the cutting action provided toward the drill tip, being the first point of contact with the material to be drilled, is relatively unaggressive, with increased cutting power and aggressiveness being provided toward the rear end of the primary cutting edge toward the body. Toward the drill tip, the gradual reduction in depth of the flute generally results in a smaller included angle between the trailing side wall of the flute and the tip face, defining a less sharp cutting edge toward the tip, contributing to the low cutting aggressiveness and efficiency compared to the rear end of the primary cutting edge which generally provides a sharper primary cutting edge due to the steeper trailing side wall of the leading adjacent flute and greater speed of travel (owing to being located a greater distance from the centre of rotation). According to the described second embodiment, providing a primary cutting edge that extends in the general manner of a variable conic helix with a decreasing helix angle, a more aggressive and powerful cutting action may be achieved right up to toward the drill tip 103. Referring to FIG. 7, this is understood to be a result, at least in part, of the fact that the rear portions of each primary cutting edge 121 rotationally lag the forward portions of the primary cutting edge 121 when the drill bit 121 is rotated in operation. Put another way, when viewed from the drill tip end of the drill tip 101 as in FIG. 7, the rear portions of the primary cutting edge 121 can be seen to "fall behind" a radial line extending from the central axis A along the front portion of the primary cutting edge 121. This particular configuration can also be seen in FIG. 7 to be akin to a ship's propeller. As a result of the configuration, at least of the second embodiment, more precise drilling of bone material in orthopaedic applications can be achieved more efficiently and more smoothly, reducing the possibility of damage to soft tissue by reducing the possibility of the radially outer portions of the primary cutting edge aggressively biting into soft tissue.

This is also enhanced by the configuration of the primary cutting edge 121 in the primary cutting edge transition region 121a, greatly reducing the aggressiveness of the primary cutting edge in the rear and radially outer portions of the primary cutting edge 111 towards the full diameter of the drill bit 101.

Figure 11:
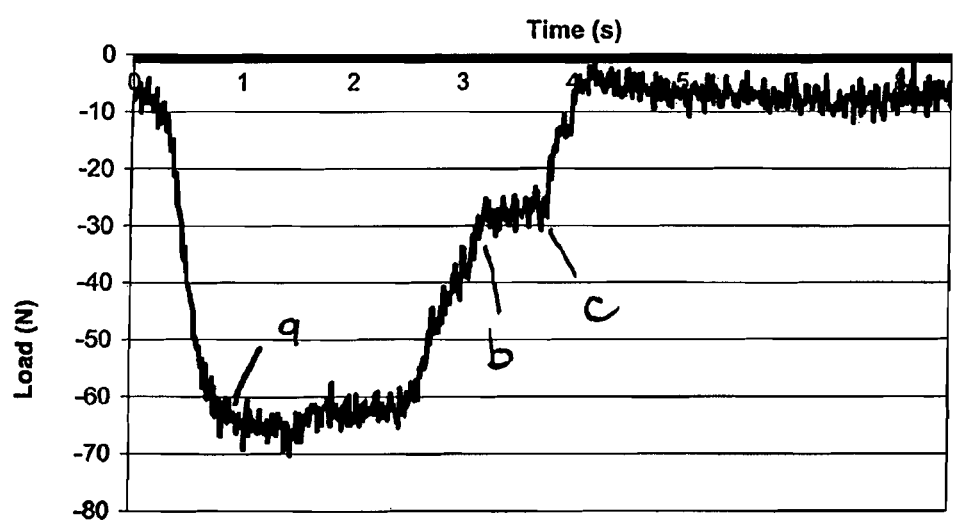
FIG. 11 is a graph depicting axial load vs time for the drill bit of FIG. 4 drilling into bone material.
Figure 12:
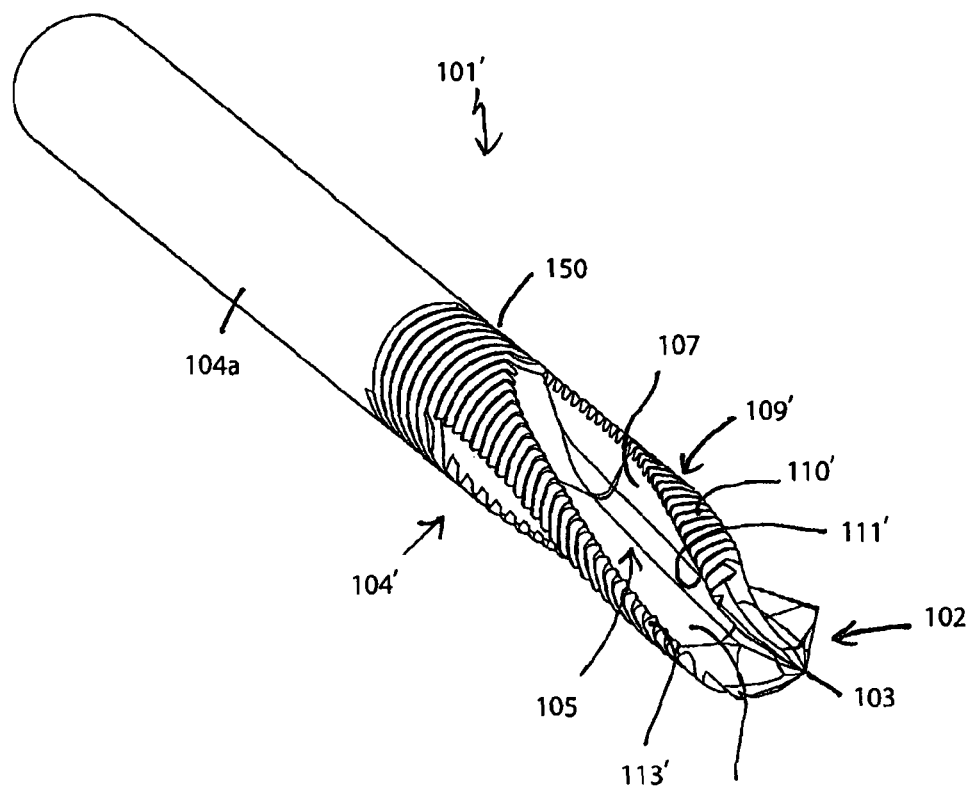
FIG. 12 is a perspective view of a drill bit according to a third embodiment.

The particular effect of the configuration of the primary cutting edge 121 of the drill bit 101 of the second embodiment can be further explained with reference to FIG. 11, which depicts the axial load against time required to be applied to a 4.5 mm prototype example of the drill bit 101 to achieve a constant axial feed rate of 5 mm/s through cortical bone material. The graph shows that the axial load applied roughly linearly increases as the drill tip 103 first engages the bone material until a peak load is rapidly achieved at point "a" (note that the load applied is depicted on a negative scale in FIG. 11) following which the load gradually reduces, believed to be in part a result of the curved configuration of the primary cutting edge 121. The drill bit 101 further advances with reducing load until the primary cutting edge transition region 121a of the primary cutting edge 121 engages the surface of the material at point "b", just prior to the drill bit advancing through to the land leading edge region 111 at full outer diameter of the drill bit. At this point, the gradual reduction in load is arrested or "braked" due to the greatly reduced cutting efficiency in the primary cutting edge region 121a of the primary cutting edge 121. The load then rapidly reduces to close to zero from point "c" where the drill bit breaks through the cortical bone. This is felt by the operator as a gradual reduction in pressure needed to be applied to the drill bit as it is advanced through the bone, with a short arrest in this load reduction providing tactile feedback to the operator to indicate that the drill is about to break through the cortical bone. The operator can use this feedback to reduce the axial load applied to the drill bit, arresting the rate of advancement of the drill bit as breakthrough is approached. Overshoot of the drill bit beyond the cortical bone into the soft tissue can thus be greatly reduced.

Figure 6C:
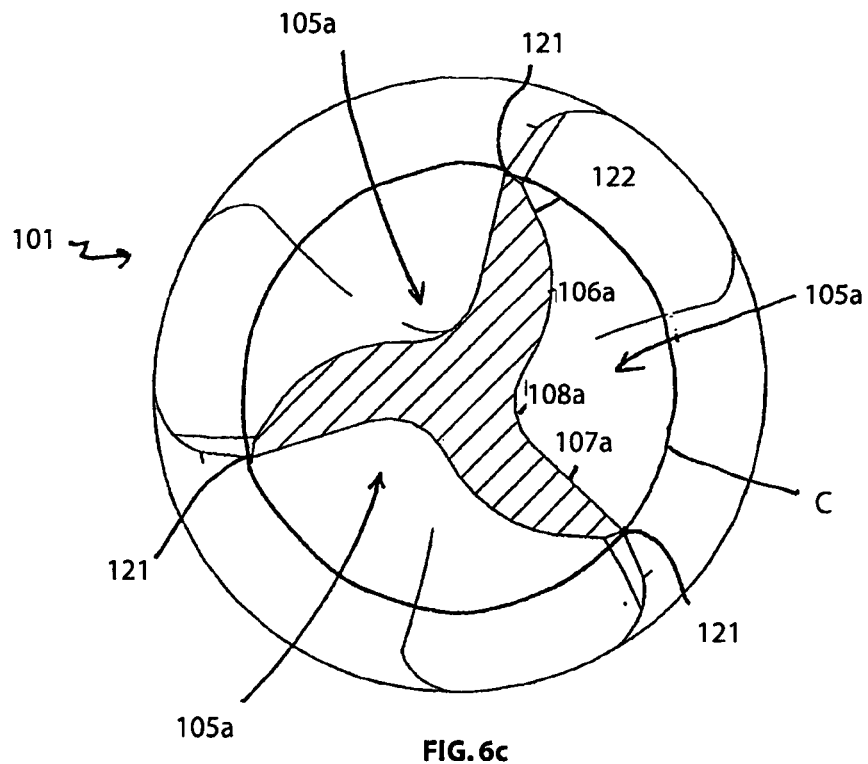
Figure 6D:
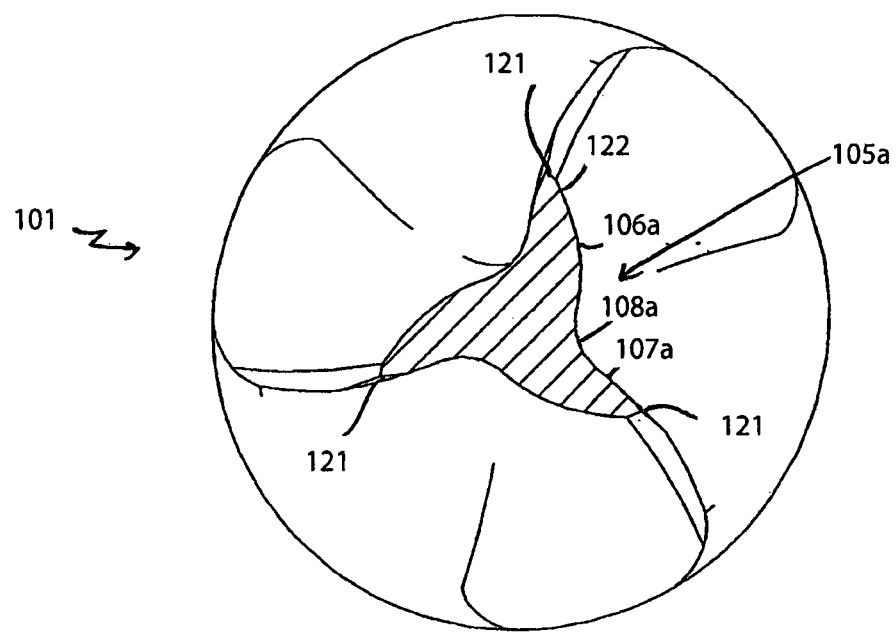
Figure 6E:
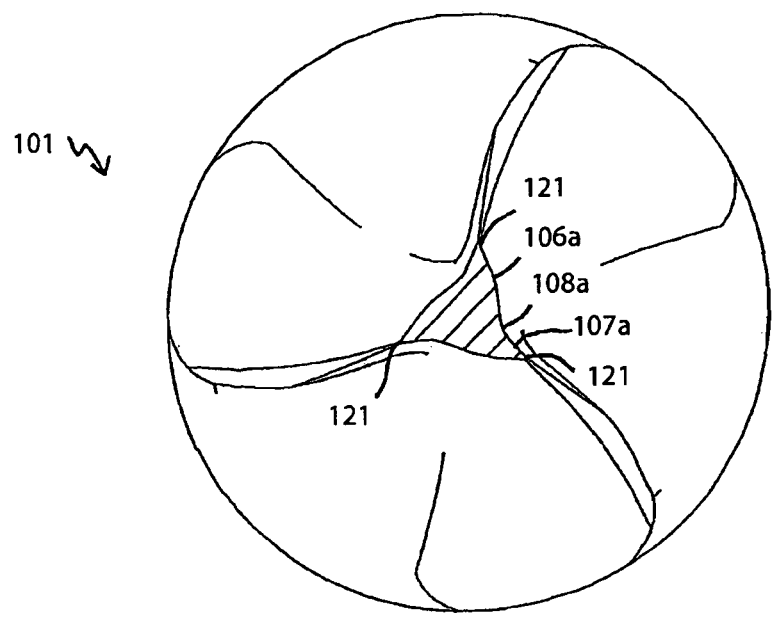

At the cutting end part 102, each tip face 114 blends into the flute leading side wall 106 of the flute 105 that is immediately trailing the tip face 114. In particular, in the arrangement of the second embodiment depicted, each tip face 114 has a leading face margin 120 which defines the primary cutting edge 121 with the adjacent flute trailing side wall 107. In the second embodiment depicted, the face margin 120 is particularly thin and is represented by a point in the cross-sections 103b through 103e. A face relief 122 extends from the face margin 120 towards the adjacent flute 105 immediately trailing the tip face 114 and smoothly blends into the flute leading side wall 106 of the trailing adjacent flute 105. Rather than blending smoothly into the flute leading side wall 107, it is also envisaged that the face relief 122 might blend into the flute leading side wall 106 by way of a series of chamfers when manufacturing capabilities are limited in their ability to grind a continuous smooth profile. As best depicted in FIG. 6c, in any cross-sectional plane extending perpendicular to the central axis A through the cutting end part 102, the face margin 122 (here effectively defined by the primary cutting edge 121) of each tip face 114 lies in a circle C extending about the central axis A and each face relief 123 lies entirely within the circle C.

As can be seen in FIGS. 6b through 6e, the depth of each flute end region 105a reduces toward the drill tip 103 and the flute base leading region 108a gradually moves closer to the primary cutting edge 121 side of the flute profile, with the flute trailing side wall end region 106a remaining relatively straight so as to maintain a relatively sharp primary cutting edge 121 toward the drill tip 103.

As with the first embodiment, the land leading edge region 111 of each land 109 is convexly curved when viewed in any transverse cross-sectional plane extending perpendicular to the central axis A of the drill bit (such as the cross-sectional plane depicted in FIG. 6a). The convex curvature may effectively be achieved by a series of discrete chamfers at the land leading edge region 111.

As with the first embodiment, for each land, the land leading edge region 111 will typically have an average radius of at least 0.2 mm. In the particular embodiment depicted, the radius of the land leading edge region 111 is approximately 0.3 mm. The radius of the land leading edge region 111 may vary in different cross-sectional planes (that is, the land leading edge region 111 again need not be formed as a constant radius arc). In any cross-sectional plane perpendicular to the central axis A extending through the body 104a, the average radius of each land leading edge region 111 would typically be at least 0.04 times the overall diameter of the drill bit.

In the particular arrangement depicted, a land transition region 113 blends the land relief 112 into the flute leading side wall 106, as best depicted in FIG. 6a, although it is again envisaged that the curved land leading edge region 111 described above may be used in conjunction with a conventional land relief/flute leading side wall. The transition region 113 will typically be curved so as to smoothly blend the land relief 112 into the flute leading side wall 106. The land transition region 113 will preferably have a radius, when measured in a cross-sectional plane perpendicular to the central axis A of the drill bit (such as the cross-sectional planes depicted in FIGS. 6a through 6e) of between 0.2 and 0.3 times the overall diameter of the drill bit 101. In the specific embodiment depicted, the drill bit 101 has an overall diameter of 4.5 mm, and the land transition region 113 has a radius of 1.15 mm. Rather than being smoothly curved, the land transition regions 113 could each be defined by one, or preferably two or more, chamfered surfaces.

The land margin 110 constitutes a part cylindrical portion of the land 109 which is not ground away from the cylindrical shaft from which the drill bit 101 is formed. The land margin 110 has a width (measured in a cross-sectional plane) of about 0.2 mm in the second embodiment depicted, however, it is envisaged that the land margin 110 may have a minimal width, effectively defined by the intersection of the land leading edge region 111 and the land relief 112. The land margins 110 each lie on a circle B extending about the central axis A and having a diameter equal to the overall diameter of the drill bit (being equal to the diameter of the shank 104 in the embodiment depicted). The land leading edge region 111, land relief 112 and land transition region 113 of each land are ground away from the cylindrical shaft from which the drill bit 101 is formed. Accordingly, at any cross-sectional plane extending perpendicular to the central axis A through the lands 109, each land leading edge region 111, land relief 112 and land transition region 113 lies entirely within the circle B as depicted in FIG. 6a. The land relief 112 is convexly curved and is typically inclined with respect to the land margin 110 towards the central axis A, defining an edge between the land margin 110 and the land relief 112. Alternatively, the land relief 112 may gradually curve inwardly from the land margin 110 towards the central axis A without leaving any definite edge therebetween. In the embodiment depicted, the land relief 112 is inclined with respect to the land margin 110, when measured in a cross-sectional plane, by about 11° degrees at the junction therebetween. As such, the land relief 112 provides a greater area between its surface and the circle B than typical prior art designs, which are generally part cylindrical with a diameter only slightly less than the overall diameter of the drill bit.

Each of the flute body regions 105b and adjacent land leading edge region 111, land transition region 113 and land relief 112 is typically formed by grinding the shaft from which the drill bit 101 is formed in a single grinding operation with a single shaped grinding wheel. The flute end regions 105a and adjacent face reliefs 122 will typically be formed in a subsequent grinding operation with a single shaped grinding wheel extending along the cutting end part 102 from a position aligned with the central axis A and located very close to the central axis A and then progressing along the cutting end part 102, moving away from the central axis A and pivoting so as to blend into the flute body region 105b with the primary cutting edge 121 extending tangentially from the secondary edge 111 at the helix angle.

A drill bit 101' according to a third embodiment is depicted in FIGS. 12 through 15 of the accompanying drawings. The drill bit 101' of the third embodiment is effectively identical to the drill bit 101 of the second embodiment described above, apart from the configuration of the lands 109, 109' and the inclusion of a thread 150 on the body 104a'. Accordingly, those features of the drill bit 101' that are identical to those of the drill bit 101 of the second embodiment described above are provided with identical reference numerals, whilst features that are modified in the drill bit 101' of the second embodiment are provided with equivalent reference numeral from the first embodiment, with the addition of an apostrophe (').

Figure 13:
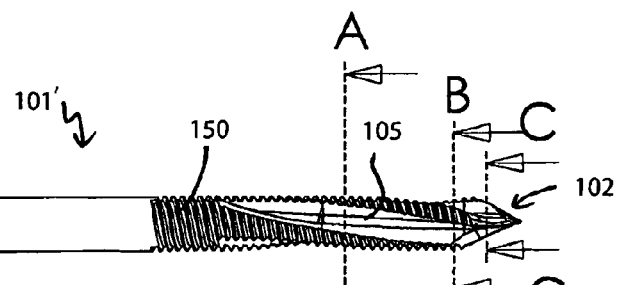
FIG. 13 is a front elevation view of the drill bit of FIG. 12.
Figure 13A:
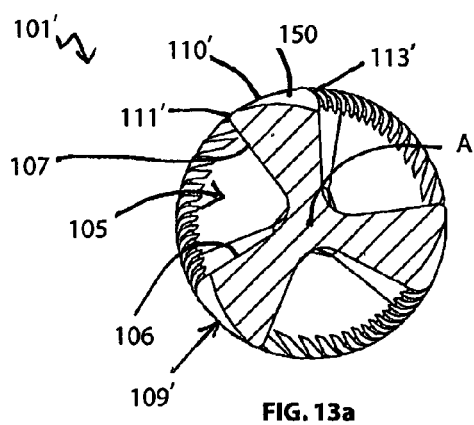
FIGS. 13a through 13c are each cross-sectional views of the drill bit of FIG. 12 taken at sections A-A to C-C of FIG. 13 respectively.
Figure 13B:
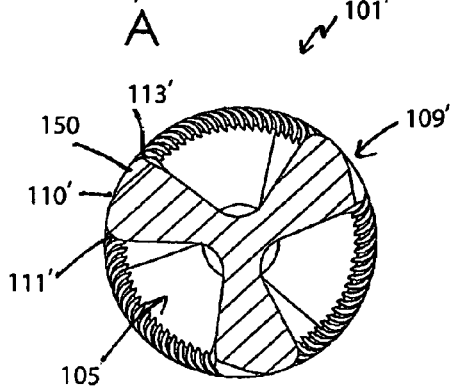
Figure 13C:
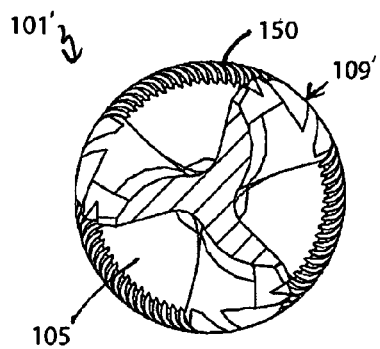
Figure 14:
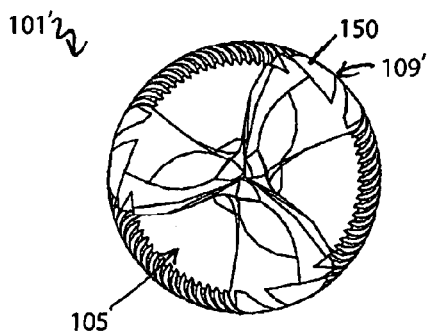
FIG. 14 is an end elevation view of the drill bit of FIG. 12.
Figure 15:
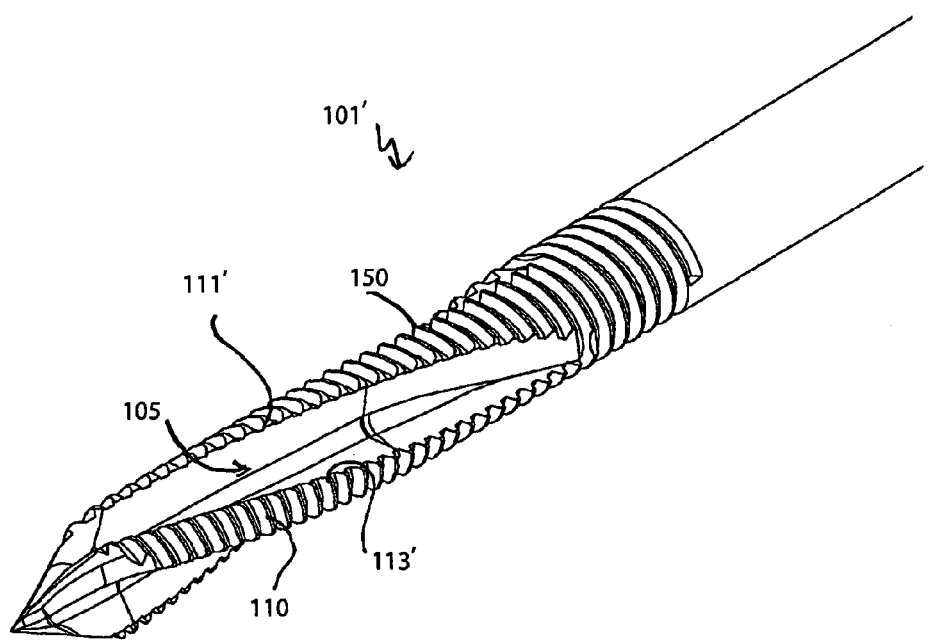
FIG. 15 is a fragmentary further perspective view of drill bit of FIG. 12.

As noted above, the lands 109' of the drill bit 101' of the third embodiment differ to the lands 109 of the drill bit 101 of the second embodiment. Particularly, the lands 109' are not provided with a land relief 112. Each land 109' has a convexly curved land leading edge region 111, and a broad land margin 110' that is maintained at full overall diameter, such that it lies on a circle extending about the central axis A and having a diameter equal to the overall diameter of the drill bit. Whilst the cross-sectional views of FIGS. 13a and 13b might at first seem to imply that the land margins 110' are narrow and there is a land relief, the inclined curve that may appear to indicate a land relief in fact reflects the recess of the thread 150 cut into the lands 109'. It can be seen, particularly from FIG. 13a that the land margin 110' extends across at least the majority of the width of each land 109'. On each land 109', a land transition region 113' blends the land margin 110' (rather than the land relief 112 as with the second embodiment) into the flute leading side wall 106 (as best depicted in FIG. 13a). Omission of the land relief, maintaining the majority of the land 109' at the full overall diameter, is particularly suitable for applications where a drill guide is utilised to guide the drill bit and only relatively short drill depths are required. Maintaining broad land margins 110' provides an increased area for contact between the drill bit 101' and drill guide, thereby reducing localised pressure between the drill bit 101' and guide if any non-axial load is applied to the drill bit 101'. This further reduces the possibility of burring or scratching of the drill guide. Adoption of a broad land margin 110' is also particularly suitable in applications where the drill bit 101' is to remain embedded in the bone into which it is drilled and act as a pin to fix an external fixator such as a cage to externally support a fracture during the healing process. In such applications, the broader land margin 110' also provides greater stability for the drill bit 101' within the bone and provides a suitably broader surface for application of the thread 150. In pin applications, the thread 150 will typically be applied to the body 104a' of the drill bit 101' from adjacent the cutting end part 102 towards (and onto) the shank 104). As can be seen in the drawings, the thread 150 extends across the full width of the broad land margins 110' for threaded engagement with the external fixator. The threads also provide for increased purchase and stability in the bone. The use of a broader land margin 110' also provides a greater second moment of inertia to the drill bit 101'. For regular drill bit applications where the drill bit is merely used to drill a hole rather than to fix an external fixator, the thread 150 would typically be omitted. Similar, in applications where the drill bit 101' is to act as a pin to locate a cutting block to a bone, the thread 150 would typically be omitted so that the (sharp) thread does not damage the cutting block.

The drill bits described above will typically be formed of stainless steel when configured for use as an orthopaedic drill bit, but other suitable high strength metallic materials may be utilised as desired to suit various applications.

The invention claimed is:

1. A drill bit having a central axis and comprising:
   a tapered cutting end part terminating in a drill tip at one end of said drill bit;
   a shank extending from an opposing end of said drill bit;
   a body extending between said cutting end part and said shank;
   a plurality of flutes formed in said drill bit and helically extending along said body into said cutting end part, each of the flutes having a flute leading side wall and a flute trailing side wall;
   a land defined on said body between each of said flutes and extending to said cutting end part, each of the lands comprising a land margin and a land leading edge region defining an intersection between said land margin and said flute trailing side wall of a leading adjacent flute;
   wherein, in substantially any body cross-sectional plane extending perpendicular to said central axis through said body, said land leading edge region of each of the lands, and said intersection defined thereby, is convexly curved.

2. The drill bit of claim 1, wherein, in substantially any said body cross-sectional plane, each of the land leading edge regions has a radius of at least 0.20 mm.

3. The drill bit of claim 1, wherein, in substantially any said body cross-sectional plane, each of the land leading edge regions has a radius of at least 0.02 times an overall diameter of said drill bit.

4. The drill bit of claim 1, wherein in substantially any said body cross-sectional plane, each of the land leading edge regions has a radius of at least 0.04 times an overall diameter of said drill bit.

5. The drill bit of claim 1, wherein each of the lands further comprises:
   a land relief extending from said margin toward a trailing adjacent said flute; and a land transition region blending said land relief into said flute leading side wall of said trailing adjacent flute;

wherein, in any of the body cross-sectional planes, said land margin of each of the lands lies on a circle extending about said central axis and each of the land leading edge regions, each of the land reliefs and each of the transition regions lies entirely within said circle.

6. The drill bit of claim 5, wherein, in substantially any of the body cross-sectional planes, said land relief is convexly curved.

7. The drill bit of claim 5, wherein, in substantially any of the body cross-sectional planes, said land relief is inclined with respect to said land margin toward said central axis.

8. The drill bit of claim 5, wherein, in substantially any of the body cross-sectional planes, said land relief is inclined with respect to said land margin towards said central axis at an angle of 5 to 15 degrees at a junction therebetween.

9. The drill bit of claim 5, wherein, in substantially any of the body cross-sectional planes, said land relief curves inwardly from said land margin towards said central axis.

10. The drill bit of claim 5, wherein, in substantially any of the cross-sectional planes, said land transition region is curved and smoothly blends said land relief into said flute leading side wall of said trailing adjacent flute.

11. The drill bit of claim 10, wherein, in substantially any of the body cross-sectional planes, said land transition region has a radius of at least 0.08 times an overall diameter of said drill bit.

12. The drill bit of claim 10, wherein, in substantially any of the body cross-sectional planes, said land transition region has a radius of at least 0.2 times an overall diameter of said drill bit.

13. The drill bit of claim 1, wherein said drill bit has three flutes.

14. The drill bit of claim 1, wherein said drill bit is an orthopaedic drill bit.

15. The drill bit of claim 1, wherein said drill bit further comprises a plurality of tip faces defined on said cutting end part and extending from one of said lands to said drill tip, said tip faces being separated by said flutes up to a forward end of each of said flutes, each of the tip faces defining a primary cutting edge with said flute trailing side wall of the leading adjacent flute;

wherein each of the primary cutting edges extends from one of said land leading edge regions, has a primary cutting edge transition region adjoining the respective land leading edge region and, in substantially any transition region cross-sectional plane extending perpendicular to said central axis through said primary cutting edge transition region, said primary cutting edge is convexly curved.

16. The drill bit of claim 15, wherein each of the primary cutting edges has a radius in said primary cutting edge transition region, measured in a transition region cross-sectional plane, that increases towards the respective land leading edge region, blending said primary cutting edge from a forward, sharp region of said primary cutting edge into said land leading edge region.

17. The drill bit of claim 1, wherein said drill bit further comprises a plurality of tip faces defined on said cutting end part and extending from one of said lands to said drill tip, said tip faces being separated by said flutes up to a forward end of each of said flutes, each of the tip faces defining a primary cutting edge with said flute trailing side wall of the leading adjacent flute;

wherein each of the primary cutting edges extends from one of said land leading edge regions, has a primary cutting edge transition region adjoining the respective land leading edge region and, in substantially any transition region cross-sectional plane extending perpendicular to said central axis through said primary cutting edge transition region, an adjoining radially outer region of said flute trailing side wall of the leading adjacent said flute is configured such that said primary cutting edge defines an increased included angle between said flute trailing side wall and the adjoining said tip face compared to a corresponding included angle in any cross-sectional plane forward of said primary cutting edge transition region.

18. The drill bit of claim 15, wherein, for each of the primary cutting edges, in an intersection cross-sectional plane extending through an intersection between each of the primary cutting edges and the respective said land leading edge region, said primary cutting edge has a radius substantially equal to a radius of said land leading edge region.

19. The drill bit of claim 18, wherein said radius is at least 0.20 mm.

20. The drill bit of claim 1, wherein each of said flutes extends to adjacent said drill tip and each of the primary cutting edges extends from one of said land leading edge regions in a variable conic helix type manner with a primary cutting edge helix angle that decreases from substantially equal to a helix angle of the respective said land leading edge region, at said land leading edge region, towards zero as it approaches said drill tip.

21. The drill bit of claim 17, wherein each of the primary cutting edges defines an included angle between said flute trailing side wall and the adjoining tip face, measured in the transition region, cross-sectional plane, that increases towards the respective land leading edge region.

* * * * *